Figure 1:
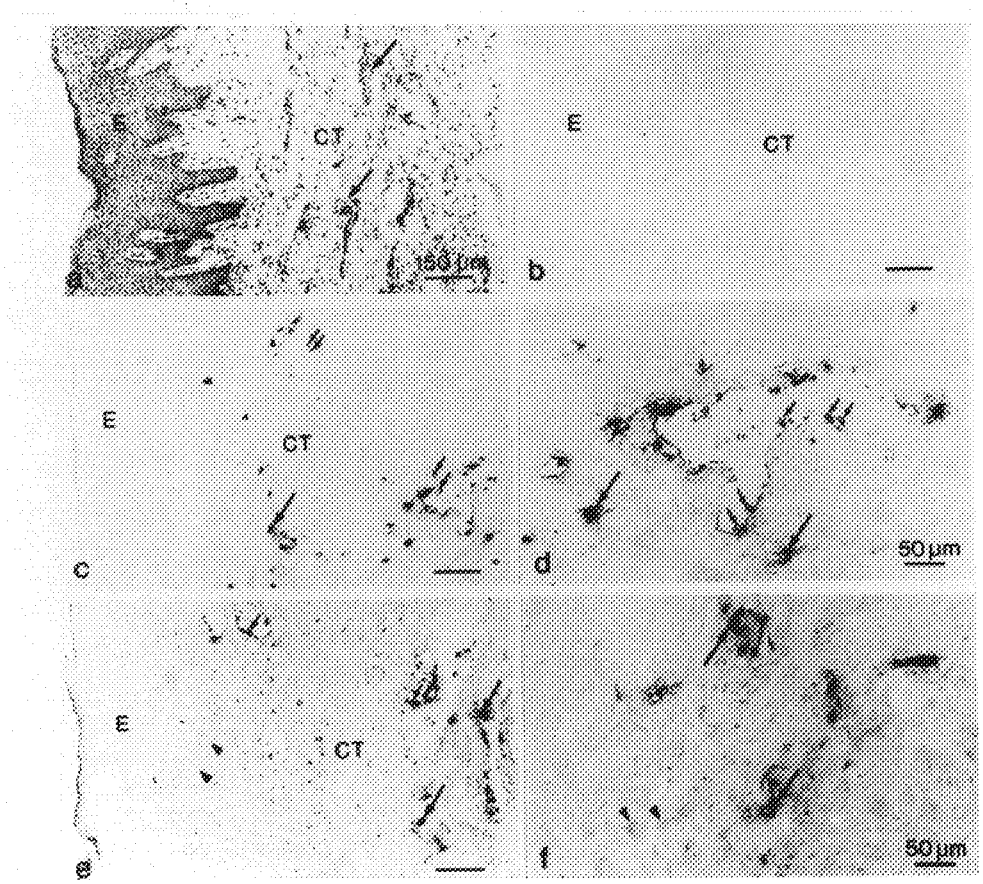

US005866432A

United States Patent [19]
Sorsa et al.

[11] Patent Number: 5,866,432
[45] Date of Patent: Feb. 2, 1999

[54] METHODS FOR DIAGNOSIS OF PERIODONTAL DISEASES

[75] Inventors: Timo Arto Sorsa; Sari Hannele Tikanoja, both of Helsinki; Leila Christina Lundqvist, Espoo, all of Finland

[73] Assignee: Oy Medix Biochemica AB, Kauiainen, Finland

[21] Appl. No.: 750,574

[22] PCT Filed: Apr. 12, 1995

[86] PCT No.: PCT/FI95/00213

§ 371 Date: Dec. 11, 1996

§ 102(e) Date: Dec. 11, 1996

[87] PCT Pub. No.: WO96/32647

PCT Pub. Date: Oct. 17, 1996

[51] Int. Cl.⁶ .............................. A01N 1/02; C12Q 1/37; G01N 33/48
[52] U.S. Cl. ............................ 436/514; 436/63; 436/811; 435/1.1; 435/7.1; 435/7.92; 435/7.93; 435/7.94; 435/7.95; 435/23
[58] Field of Search ....................... 436/63, 811; 435/1.1, 435/7.1, 7.92, 7.93, 7.94, 7.95, 23, 16, 15, 810

[56] References Cited

U.S. PATENT DOCUMENTS

| | | |
|---|---|---|
| 4,981,787 | 1/1991 | Baram . |
| 5,047,328 | 9/1991 | Chambers et al. . |
| 5,212,059 | 5/1993 | Schwartz et al. . |
| 5,627,034 | 5/1997 | Gould et al. . |

FOREIGN PATENT DOCUMENTS

96/07103  3/1996  WIPO .

OTHER PUBLICATIONS

T.Teng, et al., "Gingival Crevicular Fluid Gelatinase And Its Relationship To Periodontal Disease In Human Subjects"., Journal Periodant Res., vol. 27: pp. 544–552, (1992).
Zahradnik, R.T et al., *Journal of Dental Research*, vol. 67, 9 Mar. 1988, abstract 1724, "Accuracy and Reliability of Chairside Assay for Sulcular Neutral Proteases".
Kjeldsen, L. et al., *Journal of Biological Chemistry*, vol. 268, No. 14, 15 May 1993, pp. 10425–10432, "Isolation and Primary Structure of NGAL, a Novel Protein Associated with Human Neutrophil Gelatinase".
International Search Report for International Application No. PCT/FI95/00213.

Blaser et al., A sandwich enzyme immunoassay for the determination of neutrophil lipocalin in body fluids. Clinica Chimica Acta, 235:137–145, 1995.
Ingman et al., Salivary collagenase, elastase and trypsin–like proteases as biochemical markers of peridontal tissue destruction in adult and localied juvenile periodontitis. Oral Microbio Immunology, 8:298–305, 1993.
Ingman et al., Elastase and alpha–1 proteinase inhibitor in gingival crevicular fluid and gingival tissue in adult and juvenile periodontitis. Journal of Periodontology, 65(7):702–709, 1994.
Ingman et al., Multiple forms of gelatinases/type IV collagenases in saliva and gingival crevicular fluid of periodontitis patients. Journal of Clinical Periodontology, 21:26–31, 1994.
Kjeldsen et al., Identification of neutrophil gelatinase–associated lipocalin as a novel matrix protein of specific granules in human neutrophils. Blood, 83(3):799–807, 1994.
Soumalainen et al., Collagenase activity in gingival crevicular fluid of patients with juvenile periodontitis. Oral Microbiology Immunology, 6:24–29, 1991.
Villela et al., Collagenolytic activity in crevicular fluid from patients with chronic adult periodontitis, localized juvenile periodonitis and gingivitis, and from healthy control subjects. Journla of Periodontology Research, 22:381–389, 1987.
Sorsa et al., Comparison of interstitial collagenases from human gingiva, sulcular fluid and polymorphonuclear leukocytes. Journal of Periodontology Research, 23:386–393, 1988.
Xu et al., The development of an assay for human neutrophil lipocaline (HNL)—to be used as a specific marker of neutrophil activity in vivo and vitro. Journal of Immunological methods, 171:245–252, 1994.
Yoshie et al., Detection of Peptidase activity from *Treponema denticola, Porphyromonas gingivalis*, and *Bacteriodes forsythus* as a means of periodontoal therapy evaluation. Periodontal Clinical Investigations, 17(1):23–28, 1995.
Periocheck information package.

*Primary Examiner*—Christopher L. Chin
*Assistant Examiner*—Bao-Thuy Nguyen
*Attorney, Agent, or Firm*—Volpe & Koenig P.C.

[57] ABSTRACT

The present invention is related to a rapid and reliable method for making chair-side diagnoses of periodontal diseases and especially for predicting the risk of progressing of the periodontal diseases. The diagnosis and prognosis are performed using an immunological test kit by which increased levels of neutrophil gelatinase-related lipocalin (NGAL) derived from polymorphonuclear neutrophilic leucocytes PMNs) is measured.

4 Claims, 1 Drawing Sheet

METHODS FOR DIAGNOSIS OF PERIODONTAL DISEASES

THE FIELD OF THE INVENTION

The present invention relates to methods for rapid, reliable, specific and sensitive chair-side diagnosis of different forms of periodontal diseases as well as peri-implantitis and HIV(+)-associated periodontal diseases and especially for predicting the risks for progression of said diseases by using test kits with which neutrophil gelatinase-associated lipocalin (NGAL) can be measured.

THE BACKGROUND OF THE INVENTION

The traditional method for determining the progression of periodontitis is to assess the degree of damage which has occurred to the periodontal tissues over a given period of time by probing. Unfortunately, as a measurement technique, periodontal probing has several sources of error which make it inexact.

Radiographs have long been used to assess the level and loss of alveolar bone around teeth. However, it is impossible to visually detect minor changes in bone. Hence, the amount of bone destruction/loss tends to be underestimated when radiographs are read in a routine fashion.

In the past decade there has been increased interest in developing, testing and refining diagnostic aids for the early detection of the presence and progression of periodontitis. It is evident that any diagnostic and/or prognostic test for progressing periodontal lesions should provide information that offers some advantage over the conventional indicators of disease.

Data from epidermiological studies have confirmed that periodontal diseases are multifactorial in nature (Armitage, G. C., CDA Journal 36: 35–41, 1993). This data indicates that periodontal diseases are caused by an infection with one or more of a handful of periodontopathogenic microbes. These organisms include *Porphyromonas gingivalis* (Pg), *Prevotella intermedia* (Pi), *Bacteroides forsythus* (Bf), *Actinobacillus actinomycetemcomitans* (Aa), *Campylobacter rectus, Fusobacterium nucleatum* and spirochetes.

Much work, without giving definitive and clear resolution, has been done to determine the specific groups of subgingival microorganisms which are most strongly associated with progressing lesions (Armitage, G. C., CDA Journal 36: 35–41, 1993). The target microorganisms have been assessed by enzyme tests, culture analysis, microscopic analysis and DNA-probes.

Gingival crevicular fluid (GCF) is an inflammatory exudate that flows into the oral cavity from periodontal pockets. It contains subgingival bacteria, inflammatory cells and a lot of different substances produced by bacteria as well as host cells present. It is an inflammatory exudate with several inflammatory reactions occuring in the adjacent periodontal tissues (Birkedal-Hansen, H., J. Periodontol. 64: 474–484, 1993). In clinical practice, GCF is easy to collect by placing filter paper strips at the pocket orifice. These features have made GCF an attractive source of potential markers for the progression of periodontitis. These markers include: 1) products associated with tissue remodeling and breakdown, 2) inflammatory mediators and 3) host cell-derived enzymes (Birkedal-Hansen, H., J. Periodontol. 64: 474–484. 1993).

One of the major features of periodontitis is the destruction of connective tissue and bone. Abundant amounts of tissue breakdown products from these tissues are released during the periodontal disease process. In cross-sectional studies, GCF collected from sites with periodontitis have been shown to contain elevated levels of hydroxyproline from e.g. collagen degradation (Talonpoika, I., Changes in the composition of gingival crevicular fluid after periodontal treatment, Thesis, Ann. Univ. Turku 142, 1994). However, longitudinal studies have not been done to determine if the presence of these substances is strongly associated with progressive lesions. It is not yet known if these products are associated with the actual periodontal tissue destruction or remodeling.

Many different inflammatory mediators are produced by periodontal tissues affected by gingivitis and periodontitis. Some of these mediators appear to play a central role in the destructive processes observed in cases of periodontitis, which has led some investigators to examine the possibility of using certain inflammatory mediators as markers for progressive lesions (Sorsa, T. et al. Arch. Oral. Biol. 35: 193S–196S, 1990), Page, R. C., J. Periodont. Res. 26: 230–242, 1991).

However, so far there are no fully developed and validated diagnostic or prognostic tests for progressive periodontitis which would assess the level of inflammatory mediators in GCF. Preliminary work has suggested that the following substances may be associated with sites afflicted with periodontitis: prostaglandin $E_2$ and tumor necrosis factor-α (Page, R. C., J. Periodont. Res. 26: 230–242, 1991). However, all these inflammatory mediators are also strongly associated with bone resorption in other parts of the body. It is likely that they are all involved in the progression of periodontitis, but additional studies are needed to determine whether they can serve as useful markers for disease progression in a clinical setting.

A great deal of work has been done on developing tests for enzymes in GCF that may be related to the progression of periodontitis. Among the host-derived enzymes present in GCF that have received the most attention are: aspartate aminotransferase and collagenase (Page, R. C., J. Periodont. Res. 26: 230–242, 1991) gelatinase (Birkedal-Hansen, H., Crit. Rev. Oral. Biol. Med. 4: 197–250, 1993 and Sorsa, T., et al., Ann. N.Y. Acad. Sci. 732: 112–131, 1994) and related neutral proteases (Teng, Y. T., et al., J. Periodont. Res. 27: 544–552, 1993) β-glucoronidase (Page, R. C., J. Periodont. Res. 26: 230–242, 1991) and elastase (Ingman, T., et al, Oral. Microbiol. Immunol. 8: 298–305, 1993). Some of these enzymes are released from dead and dying cells of the periodontium, some come from polymorphonuclear neutrophils (PMN), and others are produced by other inflammatory cells (PMNs/monocytes/macrophages), epithelial and connective tissue cells at affected sites (Sorsa, T., et al., Arch. Oral Biol. 35: 193S–196S, 1990, Birkedal-Hansen, H., et al., Crit. Rev. Oral. biol. Med. 4: 197–250, 1993, Sorsa, T., et al. Ann. N.Y. Acad. Sci. 732: 112–131, 1994).

Aspartate aminotransferase (AST), formerly called glutamic oxalotransferase (GOT), is released by dead and dying host cells. In medicine, it is a useful marker for the cell death that occurs in cardiac muscle after a myocardial infarction or in the liver during hepatic disease. In fact, it is released from the dead cells of virtually all tissues of the body. Results from several longitudinal studies of patients with progressive periodontitis, in which increased clinical attachment loss was used as the criterion for progression, suggest that GCF AST levels might serve as a marker for disease progression on a site-by-site basis (Page, R. C., J. Periodont. Res. 26: 230–242, 1991). A rapid chair-side test for the enzyme in GCF has been developed. AST, based on enzymatic activity determinations, is also somewhat elevated at sites with gingivitis and nonprogressing periodontitis. Therefore, it remains to be established whether its GCF levels can usefully distinguish between inflamed sites that are breaking down and those which are not (Page, R. C., J. Periodont. Res. 26: 230–242, 1991). Thus, the use of an AST assay does not give an unambiguous diagnosis of periodontitis. Additionally, the enzymatic assay is inexact due to possible AST derived from blood contaminating the GCF.

Polymorphonuclear neutrophilic leukocytes (PMNs) are prominent inflammatory cells found in GCF from sites with gingivitis or periodontitis. They are the first line of defense against bacteria that colonize periodontal pockets. PMNs release a wide range of lysosomal and subgranular enzymes, inflammatory mediators and proteinases when challenged by bacteria. The logic behind the idea that some of these enzymes might serve as markers for the progression of periodontitis is simple. That is, when periodontitis progresses, subgingival bacteria overwhelm local host defenses (including PMNs) and lysosomal enzymes, proteases/inflammatory mediators from dead neutrophils are released into the GCF in abundance. A rapid chair-side test for a group of the lysosomal enzymes (i.e. neutral proteases) has been developed (Periocheck™)). They have been shown to be elevated in GCF from sites with advanced periodontitis (Teng, Y. T., et al., J. Period. Res. 27: 544–552, 1993). However, Periocheck™) is not sufficiently specific for PMN proteases and microbial proteinases can well degrade the substrate included into it. Neither has it been longitudinally tested to determine if it can identify sites that are at an increased risk for progression.

Preliminary work from one longitudinal study has shown that GCF levels of another lysosomal enzyme, β-glucuronidase, were elevated in patients in whom increased clinical attachment loss was detected over a one-year observation period (Armitage, G. C., CDA Journal 36: 35–41, 1993, Page, R. C., J. Periodont. Res. 26: 230–242, 1991). Lower levels of the enzyme were found in patients with nonprogressing disease. However, no rapid chair-side test for β-glucuronidase in GCF has been developed and further it remains to be determined, whether a rapid chair-side GCF test for β-glucuronidase can be developed into a useful method for detecting, on a site-by-site basis, the progression of periodontitis.

Elastase is one of the prominent neutral serine proteinases released into GCF by PMNs. However, it is known that other cells produce said enzyme (McCullough, C. A. G., J. Clin. Periodontol. 21:. 497–506, 1994). A rapid chair-side test for the enzyme in GCF has been developed based on enzymatic activity and partially tested in a clinical setting (McCullough, C. A. G., J. Clin. Periodontol. 21: 497–506, 1994). Longitudinal studies of patients with untreated periodontitis, in whom additional bone loss as detected by subtraction radiography was used as the criterion for progression, have suggested that elevated elastase levels in GCF are strongly associated on a site-by-site basis with the progression of periodontitis (McCullough, C. A. G., J. Clin. Periodontol. 21: 497–506, 1994). It was found that sites with high GCF elastase levels were more likely to develop additional bone loss within six months than sites with low levels of the enzyme (McCullough, C. A. G., J. Clin. Periodontol. 21: 497–506, 1994).

Although enzymatic GCF-based tests appear to be promising, much more work needs to be done before they have been fully and specifically tested and validated.

The tests developed so far and based on PMN-proteins especially elastase lack specificity; elastase is assayed by a synthetic protease substrate (SAAVNA-peptide) that lacks specificity, since it can be efficiently degraded by both human and bacterial peptidases/proteases/proteinases. Thus, a positive result in the enzymatic test may be obtained (Sorsa, T., et al., J. Periodont, Res. 22: 375–380, 1987; Ingman, T. et al., Oral. Microbiol. Immunol. 8: 298–305, 1993) even if no elastase is present in the tested sample. Such a test cannot be regarded as being conclusive for a diagnosis of the progression of periodontic disease.

In the Finnish patent application FI 943939 novel methods and test kits for a rapid and reliable, chair-side diagnosis of active periodontal disease related to bone destruction/and loss based on the determination of active human matrix metalloproteinase-8 (MMP-8)-neutrophil collagenase are described. In said patent application FI 943939, the entire disclosure of which is enclosed herein by reference, also other more conventional methods for diagnosing periodontal disease activity are extensively discussed.

Naturally, it is very important to be able to make a reliable diagnosis of the active disease with a chair-side test. For the prevention of periodontitis, it is, however, very important to be able to make a reliable prognosis for the progress of the disease, preferably by a chair-side test performed by the dentist in his office.

Kjeldsen L., et al. (J. Biol. Chem. 268: 10425–10432, 1993) have recently described the purification, characterization and primary structure of a novel neutrophil gelatinase-associated lipocalin (NGAL) from human peripheral blood PMNs. NGAL is a 25 kD protein associated with human PMN 92 kD gelatinase, i.e. matrix metalloproteinase-9 (MMP-9). Activated PMNs degranulate the 25 kD NGAL mostly from the secondary PMNs (specific) granules (Kjeldsen, L. , et al., J. Biol. Chem. 268: 10425–10432, 1993). Outside the PMNs NGAL can form covalent 120 kD complexes with 92 kDa MMP-9 degranulated from the PMN tertiary or C-type granules ((Kjeldsen, L., et al., J. Biol. Chem. 268: 10425–10432, 1993). This NGAL/MMP-9-complex formation explains the 120 kD form of MMP-9, which is unique for PMNs and their gelatinase (MMP-9) (Sorsa, T., et al., Arch. Oral Biol. 35: 193S–197S, 1990, Kjeldsen L., et al. (J. Biol. Chem. 268: 10425–10432, 1993). In addition, NGAL exists in a monomeric 25 kD and a dimeric 46 kD forms, which both can be exocytosed upon PMN activation (Kjeldsen, L., et al., J. Biol. Chem. 268: 10425–10432, 1993). NGAL has no modulatory actions on gelatinase, and the function of NGAL has not yet been completely clarified.

PMNs are the major sources of metallomatrix proteins (MMPs) (Sorsa, T. et al. J. Periodont. Res. 23: 380–393, 1988, sorsa, T., et al. Ann. N.Y. Acad. Sci. 732: 112–131, 1994, Golub, L. M., et al., J. Clin. Perio. 22: 100–109, 1995) and factors related to them, such as NGAL and consequently of the specific 120 kD complex NGAL/MMP-9 especially in periodontitis. Though GCF from periodontitis sites of HIV (+)-patients have been shown to contain increased amounts of active PMN derived MMPs (Salo, et al., Ann. N.Y. Acad. Sci. 732: 476–478, 1994), it has not previously been shown that these PMN derived proteins include NGAL, too. No reliable chair-side tests have been developed for indicating the progression of periodontitis based on PMN derived proteins.

Although, a vast amount of work has been done to provide a satisfactory method for diagnosing the progression of periodontitis, none of the developed and suggested solutions seem to be conclusive enough. To the present day, therefore, the clinician is still forced to rely heavily on the old conventional methods of assessing periodontitis and gingivitis by local probe measurements and radiographs. Moreover, none of the tests developed so far are capable of indicating a risk of periodontal disease at any degree. They are rather based on assessing elevated enzymatic activities in the mouth, which elevated activities may well be caused by quite different sources, such as tonsillitis, Sjögren syndrome, etc. In other words the enzymatic tests described above do not unambiguously show that the actual and only cause of the elevated amounts of the enzyme activities is periodontal diseases. The elevated amounts might be caused by bacteria as well.

A mature disease is, as already pointed out above, often discernible by the clinician with the naked eye. The need in the art is to obtain a rapid sensitive and exact way of assessing an increased risk for a progressing periodontal disease before any visual signals are available.

There is also a clear need among dentists to obtain a sensitive, specific and rapid test for chair-side assessing how far a diagnosed periodontal disease has progressed and, later on, to monitor and assess the effects of periodontal treatment.

The present inventors have now realized that the long felt need in the art can be satisfied by providing an assay which is capable of giving a warning of an increased risk of periodontal disease and indicating the level of progression of such a disease at an early stage by monitoring the existence of activated PMNs by specific immunochemical means. Some of the previously known PMNs marker proteins such as MMP-9, elastase and myeloperoxidase are not sufficiently specific, because they can be produced by bacteria (elastase) and other cells (monocytes/macrophages) and epithelial cells produce myeloperoxidase and MMP-9 as well. According to the invention there is provided a rapid immunological test for a chair-side detection and determination of a new specific PMN marker protein, i.e. NGAL from GCF of a patient for making the diagnosis and a proper prognosis of the risks for developing a periodontal disease. Said NGAL is assessed with the aid of an immunological chair-side kit from a GCF sample taken from the patient or a saliva or mouth-rinse sample from said patient. According to the invention said NGAL serves as a biochemical adjunctive marker to monitor the course and treatment of different forms of periodontal diseases including HIV(+)-infection associated periodontitis and peri-implantitis as well as to control periodontal and peri-implant health. NGAL is especially useful because it indicates the risk at an early stage of inflammation and not only the active disease and its specificity is not disturbed by the fact that NGAL sometimes forms complexes with MMP-9.

Thus, the objective of the present invention is to provide methods for making a rapid, specific and reliable diagnosis and predicting and assessing different forms of periodontal diseases and especially the risks for said diseases by a rapid, reliable chair-side test based on the determination of a specific PMN marker, NGAL, by using specific immunochemical methods. The present invention also provides test kits, which can be used in said methods to make a diagnosis and prognosis at an early stage of the disease.

THE SUMMARY OF THE INVENTION

The present invention relates to a diagnostic method for monitoring especially the risk for periodontal diseases by detecting the presence of activated PMNs in a gingival crevical fluid (GCF) sample by using a specific PMN marker protein, NGAL, which is detected with the aid of monoclonal antibodies recognizing said NGAL.

The present invention especially relates to a chair-side test kit for detecting and predicting the risk of the progression of periodontal diseases. The chair-side test kits according to the present invention comprise at least one monoclonal antibody, which specifically recognises NGAL.

In addition to the monoclonal antibody, which recognises the marker also optional polyclonal antibodies raised against NGAL can be used for constructing specific test kits.

The test kit according to the invention also contains the optional detectable direct or indirect labels and the optional solid or liquid carriers, which are needed for performing the immunological test chosen. The chair-side test kit is constructed so that it can detect said NGAL, which is a PMN marker protein, in a reliable easily interpretable way.

The present invention also relates to methods for diagnosing, predicting and assessing the different forms of periodontal diseases, as well as HIV-infections/AIDS-related periodontitis and peri-implantitis and especially the risk for progression of said diseases. The detection methods are performed as immunological assays.

According to another embodiment of the present invention the risk for periodontitis and peri-implantitis is predicted by using a chair-side prescreening test of a salivary sample or a mouth-rinse sample.

Positive cases are followed up by site-specific methods, wherein the collecting of the sample is performed with a solid, absorbing sampling device, which in the preferred embodiments of the present invention comprises the immunological assay, as such.

NGAL is especially useful for this pupose, because it indicates the risk at an early stage of inflammation and not only the active disease and its specificity is not disturbed by the fact that NGAL sometimes forms complexes with MMP-9.

The specific features of the present invention are disclosed in the claims which herewith are incorporated into the specification.

A BRIEF DESCRIPTION OF THE DRAWING

FIG. 1 (a): Histological staining of frozen sections of human alveolar mucosa containing NGAL.

FIG. 1 (b–f): Immunochemical stainings of frozen sections of human alveolar mucosa containing NGAL.

FIG. 1 shows the histological (a) and immunochemical (b–f) stainings of frozen sections of human alveolar mucosa containing NGAL. The surface epithelium is indicated by (E) and the connective tissue by (CT) in (a–c) and (e). The bar is 150 $\mu$m in (a–c) and (e) and 50 $\mu$m in (d) and (f). Perivascular inflammatory cells are shown by (arrows) in thee connective tissue. Clear immunostaining for MMP-9 (c, d) and NGAL (e, f) is seen in association with neutrophilic granulocytes (PMNs). Small arrows in (c–f) point to intravascular neutrophils (PMNs) and tall arrows point to extravasated (PMNs). As seen in the magnification (d, f) the PMNs where located intravascularly, show cytoplasmic immunoreactivity, and where extravasated, the staining reaction extends to nearby connective tissue. Barely detectable reactivity of NGAL (e) is also present throughout the connective tissue and in the basement membrane zone (arrowheads) and (f) in some fibroblasts (arrowheads).

DEFINITIONS

In the present context by the wording "NGAL" is meant neutrophil gelatinase associated lipocalin in its different forms including monomeric and dimeric NGAL as well as the NGAL/MMP-9 complex.

With the term "periodontal diseases" is in this context meant different forms of peridontitis and peri-implantitis as well as HIV(+)-infection/AIDS-disease related periodontal diseases.

By the term "diagnosis" is in the present context meant an assessment or evaluation made by a practicing dentist based on a determination or assay made with a test kit.

By the term "prognosis" is in the present context meant the assessment or evaluation made by a practicing dentist for predicting the progression of the disease—the disease pattern—including monitoring of the course and treatment of different forms of periodontal diseases and peri-implantitis as well as the control and follow-up of periodontal and peri-implant health. No prognosis can be made on a healthy person.

By the term "chair-side" is meant a diagnosis or prognosis which can be made by the practicing dentist with a test kit in the dentist office by the dentist's chair.

By the term "sampling device" usually a filter paper strip is meant, but also other solid absorbing sticks as well as the test device itself can be used as a sampling device. For saliva samples and mouth-rinse samples no specific sampling devices are needed.

THE DETAILED DESCRIPTION OF THE INVENTION

The present inventors have found in immunohistochemical and histological evaluations that the source of the MMP-9 and NGAL in inflamed human gingiva uniequivocally was PMNs. They also found that more PMN-derived MMP-9 and NGAL immunoreactivities were seen in adult periodontitis (AP)—a more PMN-related form of periodontitis in relation to localized juvenile periodontitis (LJP) gingival tissue specimens. Based on these findings the inventors will develop the test kit of the present invention for reliable diagnosis of and reliable prognosis for periodontal diseases from inflamed gingiva at an early stage of the disease.

It has also been shown by the inventors that oral/gingival keratinocytes produce both MMP-9 and NGAL in vitro. However, no MMP-9/NGAL positive signals are detected in monocyte/macrophages or in gingival/oral and sulcural epithelium in vivo. This indicates that the only source of NGAL and MMP-9 is PMNs in GCF. Both proteins are produced in vivo and they are specifically derived from PMNs in periodontitis sites and not from other cells, such as epithelial cells or keratinocytes. This is a further basis for creating a reliable test kit, which uses NGAL as a specific PMN marker protein for predicting especially the risk of developing periodontal diseases.

Furthermore, the recorded findings (FIG. 1 and the results in Example 1) indicating that when PMNs are in the lumina of the blood vessels in inflamed gingival connective tissue both MMP-9 and NGAL are located in the PMN cytoplasm, and when PMNs are extravasated into the gingival connective tissue both MMP-9 and NGAL are consistently found in the vicinities of the PMNs. This strongly suggests that PMNs are triggered during the periodontal/gingival inflammation and the triggered extravasated PMNs consequently degranulate its proteins factors, such as MMP-8, MMP-9, elastase and NGAL as well as other factors such as myeloperoxidase and elastase in the gingival connective tissue. The presence of MMP-9 and NGAL in gingiva seem to be associated with the gingival/periodontal inflammation since no MMP-9 or NGAL immunoreactivities were detected in the pulpal connective tissue from unerupted teeth free of inflammation.

In conclusion, based on the present immunochemical and functional data PMNs are considered to be the relevant source of MMPs and factors related to them (NGAL) especially in AP. Their roles may be less significant in other forms of periodontal diseases such as LJP. Also GCF from periodontitis sites of HIV(+)-patients have been shown to contain increased amounts of active PMN derived molecules, e.g. MMP-8 and MMP-9 (Salo, T., et al., Ann. N.Y. Acad. Sci., 732: 476–478, 1994).

The studies performed by the present inventors consequently indicate that PMN-derived NGAL in its different forms when assessed immunologically using a chair-side kit from gingival crevicular fluid (GCF) serves as an exact and reliable biochemical adjunctive marker for monitoring site-specifically the course and the treatment of periodontal diseases as well as to control periodontal health.

Thus, a chair-side test kit for the rapid, sensitive and selective diagnoses of periodontal diseases according to the present invention can be created. The kit may contain one or more NGAL-recognizing antibodies, but it is preferred that it contains at least one monoclonal antibody, which recognizes NGAL in its different forms and at least one detectable label, which may be attached to the antibody or added separately to the test kit. It can as well as be attached to an optional solid or liquid carriers.

The method of making the diagnosis and prognosis basically comprises the steps of collecting samples which preferably should be blood free and contacting the samples with at least one monoclonal or polyclonal antibody, which specifically recognizes the specific NGAL. Said antibody is incorporated into the test kits in an appropriate way. The binding of the NGAL to said antibody is detected and used for interpreting in the diagnosis.

The preferred monoclonal antibodies can recognize NGAL in its free form or complexed to MMP-9. In other words, the monoclonal antibody should preferably be directed to an epitope, which is not disturbed by the complex formation with MMP-9. The cell lines are produced by conventional hybridoma techniques followed by screening for cell lines which produce the desired types of monoclonal antibodies required in the test kits and methods of the present invention.

Polyclonal antibodies recognizing NGAL are obtainable by affinity purifications of gelatinase antibodies raised against gelatinase or MMP-9 (Kjeldsen, L., J. Biol. Chem. 268: 10425–10432, 1993).

The monoclonal antibodies, which recognize NGAL, are obtainable by conventional methods, which comprise the following steps. At first, mice are immunised with NGAL, which can be a crude or highly purified preparation. Hybridoma cell lines are produced by conventional hybridoma techniques using spleen cells of mice which are tested for NGAL antibody production and screened for finding different types of monoclonal antibodies. The most desired monoclonal antibodies recognise NGAL and they are sensitive and have a minimal cross-reaction with other proteins or enzymes which are present in crevicular fluids from patients with periodontal diseases.

Different types of test kits can be constructed to best suit the immunological method which is preferred and has been selected. The method is preferably chosen among immunochromatographic methods, immunometric methods, radioimmunoassays, radioimmunometric assays, enzyme immunoassays, fluoroimmunoassays, luminescence immunoassays, immmunoagglutination methods, hemagglutination methods, inhibition of agglutination methods, turbidimetric immunoassays and nephelometric immunoassays. The detectable labels and optional carriers are selected according to the appropriate method.

Most of the known immunological assays are applicable in the test. Such assays are well known to those skilled in the art and they are therefore not described in detail herein. The most preferred rapid assay mode is based on immunochromatographic methods involving the lateral flow principle as well as immunochemical methods based on the flow-through principle. Applicable methods are described, for instance in the patents EP 291 194 B1, EP 212 599 B1 and WO 94/00765 the disclosures of which are incorporated herein by reference. There is a multitude of other known methods which are as applicable as those mentioned above.

The method for diagnosing the periodontal disease or risks for progression of the disease is essentially performed as an immunological assay including the following steps. At first a gingival crevicular fluid (GCF) sample is collected with a sampling device, which ususally is a filter paper strip, from which the sample can be extracted into the test device. Optionally, the sampling device could be used as the test device, too. Simple solid devices can be used for collecting site-specific samples. After sampling, the sample is contacted with at least one monoclonal antibody, which is already attached to the sampling or test device or can be added to the test device. Alternatively, the sampling device can be added to or put on the test device, or the sample extracted from it into the test device, which contains the monoclonal antibody, which recognises NGAL.

In the most preferred method the risk for periodontal disease is detected by a site-specific method in which the sample is collected with a solid, combined sampling and test device.

According to one embodiment of the method of the invention the risk for periodontal disease can be prescreened by testing for an increased level of NGAL in a salivary sample or a sample collected with the aid of a mouthrinse. The prescreening of periodontal disease can be performed as an immunological assay using the following steps. A sample containing saliva or a mouth-rinse sample is collected by any method and the sample is then contacted with at least one antibody, which recognises NGAL in its different forms.

An increased level of said NGAL can be detected with the aid of an immunological method. Kjeldsen, L., et al. has described an ELISA-test for MMP-9 in European Journal Haematology 49: 180–192, 1992. The inventors have shown that an elevated level of NGAL can be determined by an ELISA-test corresponding to the ELISA-test described by Kjeldsen, L. The level of NGAL in a site-specific sample of GCF for healthy persons can be as low as zero, whereas a NGAL level of about 50–100 ng/ml is an indication that something is going on in the GCF. A person with a periodontal disease has significantly higher levels of NGAL in his NGAL-sample. In a direct site-specific sample of GCF a level of 50–100 ng/ml indicates that there is a risk for progression of periodontal diseases. In a salivary sample the corresponding levels are never zero. The level of NGAL in saliva is the sum of GCF from several teeths. The basic level of NGAL for a healthy person can be as high as 50–100 ng/ml in a saliva sample. A level of 150 ng/ml indicates that there is a risk for progressing periodontal diseases, whereas persons with periodontal diseases might have NGAL levels as high as 400–500 ng/ml determined by the ELISA-test mentioned above.

Therefore, values of above approximately 50 and 150 ng/ml in GCF and saliva respectively are regarded as indicators of increased levels of NGAL. The absolute values can vary depending upon several factors, such as the type and concentration and affinity of the antibody, sampling methods etc. The most important factor is, however, that the ratio between healthy and inflamed samples is about the same independent of the absolute values obtained.

The methods and materials used to develop the test kits and the methods of the present invention are discussed in more detail in the following examples.

EXAMPLE 1

Demonstration of increased amounts of NGAL in inflamed human gingival crevicular fluid (GCF) and saliva from periodontitis patients in comparision with healthy adults Patients The patients, who participated in the study were referred to the Department of Periodontology, University of Helsinki for periodontal treatment. The adult periodontitis (AP) group (n=10) included 6 women (age range 32–47 years) and 4 men (age range 35–42 years). The localized juvenile periodontitis (LJP) group (n=11) included 8 women (age range 18–21 years) and 3 men (age range 17–21 years). The systematical healthy control (n=10) group consisted of female (n=6) and male (n=4) dental students (age range 20–25). The control group had no clinically and roentgenologically detectable signs of periodontal diseases). The clinical criteria of AP was judged from standard measurements of pocket depths, radiographic loss, visible plack index and bleeding after probing as described.

Gingival crevicular fluid (GCF) and salivary sample collection

Before collecting the GCF and salivary samples, the subjects rinsed their mouths with tap water and chewed paraffin for 30 seconds. All supragingival plaque was removed before taking the GCF sample with filter paper strips (Periopaper GCF strips; IDE Interstate, Amituville, N.Y., U.S.A., which were inserted into the orifice of the gingival crevice of periodontally healthy controls as well as AP and LJP patients until mild resistance was felt. The paper strips were left in place for 30 seconds. The strips were removed and eluted with neutral physiological salt buffers. Whole saliva was collected and used for NGAL-determination.

Gingival tissue specimens

Gingival tissue specimens from various aspects of marginal gingiva, sulcular pocket epithelium obtained from upper and lower permanent teeth were taken from seven AP patients, upon routine periodontal flap surgery operations and gingivectomies performed in order to eliminate deep (>5 mm) periodontal pockets after non-successful conventional periodontal treatment comprising scaling and root planing. Likewise, gingival tissue specimens from 6 LJP patients were obtained for immunohistochemical analyses. For comparison, oral/dental tissue completely free from inflammation, fully developed, unerupted upper third molar teeth were surgically removed from young adults for valid clinical reasons, and the pulp tissue was analysed as described below. In association with the removal of the unerupted third molars, tissue specimens from the underlying normal-appearing alveolar mucosa were taken from these patients.

Preparation of the tissue specimens for immunohistochemical staining

Immediately after surgery, the soft tissue specimens were placed on a piece of cork, embedded in Tissue-TEK II O.C.T. embedding medium (Miles Laboratories Inc., Naperville, Ill. U.S.A.) and frozen with liquid nitrogen. Sections, 6 µm thick, were cut with a cryotome, collected on 3 aminopropyltriethoxysilane (Sigma, ST. Louis. Mo., U.S.A.) -coated slides to improve adhesion, and preserved at 20° C. until used. The extracted teeth were also immediately frozen in liquid nitrogen, embedded in viscous aqueous Na-carboxymethylcellulose (Fluka, Buchs, Switzerland), and transversely cut at about 15 µm thickness. To inhibit disintegration of the tissue, the sections were collected on an adhesive tape, air-dried overnight at −20° C., fixed with 99% cold methanol for 30 minutes and again air-dried. To avoid drying of the tissue during the preservation (at −20° C.) the sections were attached to transparent film.

Immunohistochemical staining

For immunostaining of the frozen mucosal, gingival and tooth specimens, Vectastain ABC rabbit Elite kit (Vector Laboratories, Burlingame, Calif., U.S.A) were used. To prevent endogenous peroxidase activity, the sections were pretreated with 0.5% $H_2O_2$ in methanol for 10–20 minutes and washed with phosphate-buffered saline (PBS) (3×10 minute). To inhibit non-specific adhesion of the antibodies during further stages of the procedure, the sections were treated with normal goat serum (1:5 dilution in PBS containing 20 mg boovine serum albumin×BSA×/ml PBS for 30 minutes, at 37° C. Antibodies were used at dilution 0.2–1 µg/ml. After 3 washes with PBS, the sections were treated with biotinylated goat antirabbit IgG, at dilution 1:250 in PBS containing 1 mg BSA/ml PBS, for 30 minutes at 37° C. The sections were again washed, incubated with 1:1 mixture of reagents A and B diluted with PBS, for 30 minutes at 37° C., stained with the ABC-stain and mounted with Glycergel (Dakopatts, Glostrup, Denmark). In order to determine the nature of any reactive cells/tissues, some sections were counterstained with hematoxylin. For a more detailed histological examination, sections (not to be immunostained) of each specimen were stained with hematoxylin and eosin.

ELISA-measurements

ELISA-measurement specific for NGAL in AP GCF and saliva were conducted as described in Kjeldsen, L., et al., European Journal of Haematology 49: 180–1992, 1992.

AP patients were found to have increased amounts (200–300 µg/ml) of NGAL in the GCF samples from periodontitis titer relative to periodontally healthy control GCF (10–50 ng/ml). Also salivary NGAL-amounts (>250 ng/ml) were increased in AP-patients; sample relative to periodontally healthy control saliva sample (50–100 ng/ml).

Results

All together the immunohistochemical and ELISA data show that the major/predominant source of NGAL in periodontitis gingiva are PMNs, and increased amounts of PMN NGAL is present in adjacent periodontitis GCF as well as in saliva. FIG. 1 shows the histological (a) and immunochemical (b–f) stainings of frozen sections of human alveolar mucosa. The surface epithelium is indicated by (E) and the connective tissue by (CT) in (a–c) and (e). The bar is 150 µm in (a–c) and (e) and 50 µm in (d) and (f).

Hematoxylin and eosin-staining shows scattered, frequently perivascular inflammatory cells (arrows) in the connective tissue underlying the parakeratinized stratified squamous cell epithelium.

In a control section treated with normal rabbit immunoglobulin fraction no staining is seen in any elements of the tissue. Clear immunostaining for MMP-9 (c, d) and NGAL (e, f) is seen in association with neutrophilic granulocytes (PMNs) (small arrows in c–f) point to intravascular neutrophils (PMNs) and tall arrows point to extravasated PMNs. As seen in the magnification (d, f) the PMNs where located intravascularly, show cytoplasmic immunoreactivity, and where extravasated, the staining reaction extends to nearby connective tissue. Barely detectable reactivity of NGAL (e) is also present throughout the connective tissue and in the basement membrane zone (arrowheads) and (f) in some fibroblasts (arrowheads).

Reactivity of NGAL in the adult as well as the localized juvenile periodontitis was clearly associated with part of the inflammatory cells comprising predominantly of PMNs, but in addition a weak staining was seen throughout the connective tissue. Encouraged by these results, the inventors are developing rapid, reliable and specific chair-side test kits based on immunochromatographic methods using monoclonal antibodies as described in the Examples below.

EXAMPLE 2

Monoclonal antibodies against NGAL

NGAL is purified as described in Kjeldsen, L., et al., J. Biol. Chem. 268: 10425–10432, 1993, which publication herewith is incorporated by reference. Monoclonal antibodies for the test of the present invention are basically developed according to the original technique of Kohler and Milstein (Nature 256: 495, 1975). The inventors however use a specific application of the technique mentioned above published by Stenman, et al., J. Immunol. Meth. 46: 337, 1981).

EXAMPLE 3

Immunisation, fusion and cloning

BALB/c mice are immunized and boosted intraperitoneally with a sample of NGAL. Mice, having an antibody titer (for test method, see Example 4 below) after the first boost, will be boosted intravenously with 50–100 µg of the antigen above in saline. The spleen is removed 3–4 days after the last booster, and spleen cells are fused in polyethylene glycol (PEG, Boehringer Mannheim Cat. no. 1243268) with myeloma cells. After fusion, cells are cultivated in microplates in RPMI 1640 medium with 7.5% horse serum. After 1 day, selective HAT medium (2% mixture of hypoxanthine, aminopterin and thymidine in RPMI-1640, Gibco 50×HAT, Cat. no. 043-01060H) is added to the cultures.

After 2 weeks of culture the cells are transferred to HT culture medium (2% HAT without aminopterin, Gibco 50×HT, Cat. no. 043-01065H), and finally 2 weeks later back to RPMI-1640+7, 5% horse serum. Antibody-producing cultures are screened and characterized (for methods, see below). The cultures of selected hybridomas are then cloned. For further characterisation, antibody is produced in mouse ascites.

EXAMPLE 4

Screening and titration

To detect antibody production against NGAL, a radioassay method is used.

Highly purified NGAL is radioiodinated with a Chloramine T method (Greenwood, F. C., et al., Biochem. J. 89: 114, 1963) and it is used as a label in the screening assay. In the assay, 50 µl of supernatant from microtiter plates is incubated with 150 µl of the $^{125}$I-label of antigen (about 10000 cpm) in a phosphate-EDTA-NaCl buffer containing 0.33% BSA, pH 7.4. After overnight incubation, bound label is precipitated by addition of 100 µl of bovine gammaglobulin in phosphate buffer and 1 ml of 20% PEG 6000 in phosphate buffer. The radioactivity of the precipitate is counted. A sample is considered positive for antibody production when the activity precipitated is significantly greater than the background (growth medium instead of culture supernatant), i.e. bound activity is more than 50% of the maximal binding of the polyclonal preparation used as a control.

When titrating, the titer is defined as the dilution binding 50% of the maximal amount of label specifically bound by a large excess of antibody. Polyclonal NGAL recognizing antibody is used as control antibody.

EXAMPLE 5
Methods of testing and characterization

The hybridoma cultures that are found positive by screening are further tested for their sensitivity to detect NGAL and MMP-9 complexed NGAL and for the most important cross-reation (i.e. MMP-9). A RIA method is used where the label is the same preparation of radioiodinated NGAL, which is used in the screening assay as well. 100 $\mu$l of label, 50 $\mu$l of standard or the cross-reactant to be tested and 50 $\mu$l of antibody solution (all in phosphate-EDTA-NaCl buffer containing 0.33% BSA, pH 7.4) are incubated overnight. Separation of bound radioactivity is performed similarly to the screening method. Each antibody is diluted to bind about 50% of its maximal binding. Standards are prepared from NGAL in concentrations ranging 1–1000 ng/ml.

The hybridomas with best sensitivity and without disturbing cross-reactions with other periodontal disease related proteins and enzymes mentioned in the background of the invention are selected to be cloned. The specificity of the new monoclones is further characterized.

For an immunometric method, an antibody pair is needed where the antibodies can bind simultaneously to the same antigen molecule. Therefore, the antibodies must recognize different epitopes of the molecule and those epitopes must be distant enough that the binding can happen without sterical hindrance causing loss of affinity. It is also important to choose a monoclonal antibody, the binding of which to NGAL is not disturbed by the complex-formation with MMP-9.

In order to select an antibody pair like this, candidate monoclones are tested in pairs to find good simultaneous binding.

EXAMPLE 6
Diagnostic test methods for predicting the risk for progression of periodontal diseases The monoclonal antibodies specific to NGAL which have been developed according to the above procedure are used for designing a variety of test methods useful in the assessment of periodontal disease activity. Alternatives for quantitative and qualitative methods are described below.

A more modern principle that can be used in a test according to this invention is the use of two antibodies in a flow-through immunometric technique (U.S. Pat. No. 4,366,241). Here, the test is best performed in a device where a pad of absorbing material is covered by a membrane made of, for instance nitrocellulose or nylon. On this membrane there is an area on which antibodies of one kind are attached. Liquid sample is pipetted on the membrane and NGAL possibly present in the sample will be bound to the antibodies the rest of the sample flowing through the membrane. Thereafter, a labelled reagent is added. This label can be a conjugate of the second antibody (monoclonal or polyclonal antiNGAL recognizing an epitope other than the first antibody) and an enzyme like horseradish peroxidase. In this case, if there is any NGAL bound on the membrane the conjugate will bind to it and can be visualized by washing off excess conjugate and adding a precipitating substrate to the label enzyme which substrate can produce a visible color. The substrate can also be one producing an invisible signal (for instance, fluorescence or chemiluminescence). Intensity of colour, fluorescence or chemiluminescence can be recorded by appropriate instruments and in these cases, if concentration calibration is used, the test result can be read quantitatively. The labelled reagent can also be a suspension of colored (or otherwise signal producing) particles (made of, for example, latex) which are coated with the second antibody. Here, the pore size of the membrane is so adjusted that those particles which are not immunochemically bound on the membrane will flow through the pores. After a washing step, the bound particles can be detected directly if visual or indirectly by signal measurement.

For designing a periodontal disease test, the immunochromatographic principle can advantageously be used. This technique, often referred to as the lateral flow technique, has been described in detail in EP 291 194 (which includes embodiments with a test device that essentially consists of a membrane and a pad of absorbing material in a hollow casing) and in WO 94/15215 (which includes embodiments with a test device that essentially consists of a membrane and an absorbing pad in a dipstick constructed with a chamber-like gap). In the immunometric version that employs two different antibodies the first NGAL antibody is coated on particles that act as a label which can be detected by the eye if the particles are colored, or by suitable instruments if they are fluorescent or chemiluminescent signal producing. The particles can be made, for example, of latex, colloidal metal (gold, selene) or a dispersing dye. These label particles are attached in a test device so that when the absorbing part of the device is brought into contact with the liquid sample and the sample is absorbed, the particles will migrate with the liquid flow and simultaneously, the labelled antibody will bind the antigen NGAL if present in the sample. The liquid will be further absorbed into the membrane in the device. On the membrane, a second antibody (monoclonal or polyclonal antiNGAL recognizing an epitope other than the first antibody) has been attached in a zone-like area. When the liquid flow carrying the label migrates through this zone, those labelled particles which have bound antigen will be bound to the zone. Thus, the zone will be detectable if there was antigen present in the sample.

This technique can also be based on the use of one antibody only. This can be done, for instance, by using antigen coated label particles in competition with the antigen possibly present in the sample. The monoclonal antibody specific to NGAL is attached in a zone on the membrane. Sample antigen will occupy the antibody binding sites in the zone and thus, no detectable zone will appear.

Immunochromatography can also be made quantitative by measuring the signal produced by a label that is bound to the membrane when known standards or unknown samples are run. Visual semiquantitation is possible if several antibody zones with increasing antibody amount in the zone are used in the test device.

The above mentioned modern techniques are useful for the development of a rapid chair-side test with a short performance time (often only a few minutes). Test version with a label directly visible to eye will provide tests that can be performed and interpreted very reliably by personnel untrained to laboratory work.

There are a multitude of techniques which are suitable if a quantitative test result is required, e.g. turbidimetric and nephelometric methods can be used. Classical immunochemical methodologies with radioisotopic labels can be applied (radioimmunoassay involving one antibody in a competetive assay design, and immunoradiometry involving an antibody pair). Instead of isotopic labels, a variety of other labeling compounds are useful in related methodologies. Enzymes like horseradish peroxidase or alkaline phosphatase can be conjugated to antibodies in order to act as labels in enzyme immunoassays or immunoenzymometric assays which labels are detected with the help of calorimetric, fluorometric or chemiluminometric substrates. Also, fluorescent compounds can be directly conjugated to antibodies and be used in fluoroimmunoassays or fluoroimmunometric assays. These methods however are not intended for a rapid chair-side test because the need specific possibly automated instrumentation and/or specially trained personnel.

EXAMPLE 7

Site specific and screening tests for determining risk of periodontal disease

All the test methods described above can in principle be used in both site-specific and screening tests. However, flow-through and immunochromatographic methods are best suited to a rapid chair-side test which is optimal in both cases. In a screening test the aim is to find out if increased total NGAL is present in a patient's saliva or mouthrinse samples.

Saliva is easily collected after letting the patient first rinse his mouth thoroughly and then chew paraffin. Other stimulants of saliva excretion can also be used. If it is necessary to store the specimen before analysis, a specific saliva collection device like Omni-SAL® (Saliva Diagnostic Systems, WA) can be used. Alternatively, the test can be performed in a mouthrinse specimen which is collected by allowing patients to chew paraffin for 30 sec–1 min and subsequently spit the oral fluid contents; thereafter, the patients rinse their empty mouths with 3 ml of tap water which is then collected for testing.

For a site-specific test, the dentist can collect a specimen of GCF by placing a filter paper strip at the periodontal pocket orifice. The strip is allowed to absorb liquid, preferably for a standardized time. Then, the strip is transferred to a test tube with an adequate buffer solution where sample proteins are extracted. In case an immunochromatographic dipstick format is used, the dipstick is directly dipped into the tube for the test. Besides the filter strips other absorbing materials like porous plastics or ceramics as well as organic or inorganic silica compounds are also applicable, probably attached to a holder for convinient transfer. Liquid can also be collected in a capillary tube of glass or plastic. Finally, a dipstick-type test device can be so designed that it includes an absorbing end that is placed in the periodontal pocket and the sample is absorbed directly into test device.

A site-specific dipstick test for ruling out the possibility of disease in the individual site or directing the clinician to further studies can be a qualitative one. The threshold value (cut-off concentration) for the test is chosen so as to give optimal sensitivity and specificity. In the case of a periodontal disease risk test, the NGAL concentrations—determined with ELISA-tests—which are above approximately (50 ng/ml) can be interpreted as positive in GCF samples. Correspondingly, in a screening test in saliva/mouthrinse, a concentration above approximately 150 ng/ml of NGAL determined with an ELISA-test may suggest an increased risk of periodontitis. This test (from saliva or mouthrinse samples) provides a new approach for finding patients with risk of periodontitis, and for detecting periodontal sites exhibiting risk for development of periodontal disease it can be used for screening populations like school children, or for special groups known to be in increased risk (for example, AIDS patients) or groups like smokers with whom diagnosis of periodontal disease is more difficult than usual.

EXAMPLE 8

Constructing a chair-side test kit for NGAL

A narrow zone of a nitrocellulose strip (strip 1, approx. 50×300 mm) is coated with a monoclonal antibody against NGAL. Concentration of antibody is adjusted low enough to enable only NGAL amounts that are above normal to cause a positive signal in the test. Coloured latex particles are coated with another NGAL antibody. The coated latex particles are dried on a zone in the middle of a strip (strip 2, approx. 50×300 mm) of absorbing polyethylene material. The diameter of the particles is small enough that they can flow freely through the pores in both strip materials. The two strips are attached on a plastic backing (approx. 50×1000 mm) so that they are in a contact which allows capillary flow of sample liquid from strip 2 to strip 1 when the end of strip 2 is dipped into liquid. For absorption of excess liquid, a pad of filter paper is attached in contact with strip 1 opposite to strip 2. The dipstick constructed is used to perform the rapid NGAL test according to the following instructions.

Performance of the immunochromatographic NGAL test:

1. One end of the dipstick (end of strip 2) is dipped into sample liquid and kept there until the liquid front has reached strip 1, and then removed from the sample.

2. During an incubation of 5 minutes the sample migrates in the strips and the latex particles are transferred with the liquid over the antibody-coated zone to the other end of the dipstick.

3. Strip 1 is inspected. If a coloured zone is formed, the result is positive.

EXAMPLE 9

The use of the chair-side test kit for monitoring the risk of periodontal diseases using monoclonal antibodies A group of five patient are screened for periodontitis at the dentist's office using the NGAL-chair-side test. Before any dental periodontal probing and/or other assessment for periodontitis, filter paper strips for collecting GCF samples (Periopaper GCF strips) are placed on the orifice of the teeth (n=5) which are believed to be affected by periodontitis. After 30 seconds the sampling strips are removed and transferred into test tubes containing phosphate buffer (1 ml). GCF in the strips is extracted into buffer. The extracts are tested with NGAL dipsticks as instructed in Example 8. A coloured zone appears in 4 of the sticks which indicates increased presence of NGAL (free or complexed with MMP-9) in the GCF extract. By further periodontal probing as well as roentenological evaluation the presence of periodontal lesions are confirmed and the positive cases, i.e. the patients showing an increased level of NGAL are followed up and are given the appropriate treatment. The effect of the treatment is surveilled in more detail for a certain period.

We claim:

1. A method for diagnosing periodontal diseases and predicting the risk for progress of said diseases, wherein the detection is performed as an immunological assay comprising the steps of:
   a) collecting an essentially blood free sample of gingival crevicular fluid (GCF) with a sampling device or collecting a saliva sample with the aid of a mouth-rinse;
   b) contacting said sample with an antibody, which binds a neutrophil gelatinase associated lipocalin (NGAL); and
   c) detecting the presence and amount of said NGAL; wherein the greater the amount of NGAL detected in step (c), the greater the risk that is indicated for periodontal disease.

2. The method of claim 1 in which a site-specific diagnosis and site-specific prediction of risk is performed by collecting the sample with a solid absorbing sampling device, wherein the test for diagnosis and risk is performed on the sampling device.

3. The method of claim 1 wherein an elevated amount of NGAL from polymorphonuclear neutrophils (PMN) cells is determined by detecting an amount of NGAL in said cells and comparing the amount obtained with samples from a healthy person, wherein the greater the amount of NGAL detected, the greater the risk that is indicated for periodontal disease.

4. The method of claim 1, wherein the amount of NGAL is determined by an immunological assay quantitatively, semi-quantitatively or qualitatively.

* * * * *